(12) United States Patent
Donald et al.

(10) Patent No.: US 9,987,464 B1
(45) Date of Patent: Jun. 5, 2018

(54) URINARY CATHETER INSERTION DEVICE AND KIT

(71) Applicant: Donaco Medical Design, LLC, Woodstock, GA (US)

(72) Inventors: Dallas C. Donald, Canton, GA (US); Robert W. Henson, Durham, NC (US); Edward P. Browka, Oneida, NY (US); Eli B. Nichols, Durham, NC (US); Adam T. C. Steege, Durham, NC (US); Darrin W. Swanson, Randleman, NC (US)

(73) Assignee: Donaco Medical Design, LLC, Woodstock, GA (US)

( * ) Notice: Subject to any disclaimer, the term of this patent is extended or adjusted under 35 U.S.C. 154(b) by 0 days. days.

(21) Appl. No.: 15/655,509

(22) Filed: Jul. 20, 2017

(51) Int. Cl.
*A61M 25/01* (2006.01)
*A61M 25/00* (2006.01)
*A61M 25/06* (2006.01)
*A61M 27/00* (2006.01)

(52) U.S. Cl.
CPC ...... *A61M 25/0136* (2013.01); *A61M 25/002* (2013.01); *A61M 25/0017* (2013.01); *A61M 25/01* (2013.01); *A61M 25/013* (2013.01); *A61M 25/0111* (2013.01); *A61M 25/0113* (2013.01); *A61M 25/0662* (2013.01); *A61M 27/008* (2013.01); *A61M 2025/0175* (2013.01); *A61M 2202/0496* (2013.01); *A61M 2202/0498* (2013.01); *A61M 2210/1078* (2013.01); *A61M 2210/1085* (2013.01); *A61M 2210/1089* (2013.01)

(58) Field of Classification Search
CPC ............ A61M 25/002; A61M 25/0113; A61M 25/01; A61M 25/013; A61M 25/0111; A61M 25/0017; A61M 27/008; A61M 2210/1078; A61M 2210/1085; A61M 2210/1089; A61M 2025/0175; A61M 2025/0496; A61M 2025/0498
See application file for complete search history.

(56) References Cited

U.S. PATENT DOCUMENTS

| | | |
|---|---|---|
| 3,854,483 A | 12/1974 | Powers |
| 4,062,363 A | 12/1977 | Bonner, Jr. |
| 4,652,259 A | 3/1987 | O'Neil |
| 4,871,358 A | 10/1989 | Gold |
| 5,417,666 A | 5/1995 | Coulter |
| 5,454,790 A | 10/1995 | Dubrul |
| 5,897,535 A | 4/1999 | Feliziani et al. |
| 6,610,005 B1 | 8/2003 | Tao |
| 6,939,339 B1 | 9/2005 | Axexandersen et al. |
| D542,914 S | 5/2007 | Tanghoj |
| 7,833,475 B2 | 11/2010 | Madsen |
| 8,066,693 B2 | 11/2011 | Tanghoj et al. |

(Continued)

FOREIGN PATENT DOCUMENTS

| | | |
|---|---|---|
| GB | 2031733 | 12/1982 |
| WO | 2009004626 | 8/2009 |

*Primary Examiner* — Jason Flick
*Assistant Examiner* — Anh Bui
(74) *Attorney, Agent, or Firm* — Louis F. Wagner; FisherBroyles, LLP

(57) ABSTRACT

A catheter insertion device which employs back-and-forth longitudinal axial movement to advance the catheter by the cooperative interface of an incline ramp and a decline ramp with a split gripping mechanism is described.

20 Claims, 17 Drawing Sheets

(56) References Cited

U.S. PATENT DOCUMENTS

| | | |
|---|---|---|
| 8,267,919 B2 | 9/2012 | Utas et al. |
| 8,703,048 B2 | 4/2014 | Nielson et al. |
| 8,728,057 B2 | 5/2014 | House |
| 8,911,424 B2 | 12/2014 | Weedock et al. |
| 8,920,403 B2 | 12/2014 | Doerr |
| 8,926,592 B2 | 1/2015 | Blott et al. |
| 8,932,262 B2 | 1/2015 | Ostfeld et al. |
| 8,939,962 B2 | 1/2015 | Azar |
| 8,945,074 B2 | 2/2015 | Buan et al. |
| 8,951,241 B2 | 2/2015 | Eberli et al. |
| 8,956,340 B2 | 2/2015 | Pearce, III et al. |
| 8,968,273 B2 | 3/2015 | Passadore et al. |
| 8,974,438 B2 | 3/2015 | Hong et al. |
| 8,979,824 B2 | 3/2015 | Amos et al. |
| 8,986,286 B2 | 3/2015 | Tanghoej et al. |
| 8,992,465 B2 | 3/2015 | Hauschild et al. |
| 8,998,882 B2 | 4/2015 | Knapp et al. |
| 8,998,883 B1 | 4/2015 | Feloney |
| 9,005,165 B2 | 4/2015 | Kalser et al. |
| 9,011,413 B2 | 4/2015 | Chung |
| 9,017,303 B2 | 4/2015 | Rackley |
| 9,023,013 B2 | 5/2015 | Schertiger et al. |
| 9,033,149 B2 | 5/2015 | Terru |
| 9,033,956 B2 | 5/2015 | Lavelle |
| 9,192,460 B2 | 11/2015 | Gandhi |
| D759,813 S | 6/2016 | Newman et al. |
| D759,814 S | 6/2016 | Newman et al. |
| 9,585,989 B2 | 3/2017 | Deal |
| 9,744,331 B2 | 8/2017 | Erbey, II et al. |
| 9,750,621 B2 | 9/2017 | Ponsky et al. |
| 2007/0161971 A1 | 7/2007 | House |
| 2013/0211324 A1* | 8/2013 | Voss ............ A61B 17/0057 604/104 |
| 2013/0226154 A1 | 8/2013 | House |
| 2014/0138951 A1 | 5/2014 | Kuczaj |
| 2014/0358127 A1 | 12/2014 | House |
| 2014/0371672 A1 | 12/2014 | Pinchuk et al. |
| 2015/0011980 A1 | 1/2015 | Tan et al. |
| 2015/0011981 A1 | 1/2015 | House |
| 2015/0018803 A1 | 1/2015 | Tjassens et al. |
| 2015/0018804 A1 | 1/2015 | Rolsted |
| 2015/0018805 A1 | 1/2015 | House |
| 2015/0025508 A1 | 1/2015 | Rolsted |
| 2015/0038947 A1 | 2/2015 | Schmid et al. |
| 2015/0051587 A1 | 2/2015 | Rolsted et al. |
| 2015/0051588 A1 | 2/2015 | Miller et al. |
| 2015/0057641 A1 | 2/2015 | Cai et al. |
| 2015/0094695 A1 | 4/2015 | Daniel et al. |
| 2015/0094696 A1 | 4/2015 | Adams, Jr. et al. |
| 2015/0105756 A1 | 4/2015 | O'Brien et al. |
| 2015/0112228 A1 | 4/2015 | Ekema et al. |
| 2015/0112312 A1 | 4/2015 | Mooney et al. |
| 2015/0112313 A1 | 4/2015 | Schertiger |
| 2015/0112314 A1 | 4/2015 | Gustavsson et al. |
| 2015/0126975 A1 | 5/2015 | Wuthier |
| 2015/0126976 A1 | 5/2015 | Tang et al. |
| 2015/0133846 A1 | 5/2015 | Kerr |
| 2015/0133898 A1 | 5/2015 | Murray et al. |
| 2015/0141965 A1 | 5/2015 | Bonham |
| 2015/0141966 A1 | 5/2015 | Gustavsson |
| 2017/0209671 A1* | 7/2017 | Ring ............ A61M 25/0113 |

\* cited by examiner

URINARY CATHETER INSERTION DEVICE AND KIT

TECHNICAL FIELD

The invention described herein is a catheter insertion device and kit, particularly useful with individuals having limited use of their extremities.

BACKGROUND OF THE INVENTION

A compact urinary catheter is described which is particularly useful for patients with limited mobility, enabling them to manage self-insertion with minimal aid from others, recognizing that this is not the sole-intended group, and that all end-users of the device, regardless of mobility limitations, are included.

SUMMARY OF THE INVENTION

A catheter insertion device is described and which includes various components: a substantially hollow housing having a longitudinal axis, the housing having a front and a rear and defining at least one longitudinal slot on a side of the housing; a first ramp positioned toward a rear of the slot, the first ramp having a decline for downward deflection; a second ramp positioned toward a front of the slot, the first ramp having an incline for upward deflection; the housing further defining a bottom longitudinal slot. The device will further have an opposed pair of impingement surfaces toward a front of the housing to assist in preventing rearward movement of an inserted catheter tube and an advancing sleeve which is longitudinally insertable along the longitudinal axis of the housing into at least a portion of the housing from the rear, the sleeve movable in a back-and-forth direction along the longitudinal axis of the housing, the sleeve having a sleeve top, a sleeve bottom, a sleeve front and a sleeve rear.

In one aspect of the invention, the sleeve will comprise: an inwardly and outwardly deflectable projection at the top front of the sleeve the inward and outward deflection occurring transverse to the longitudinal axis of the advancing sleeve; a bottom rail on the sleeve configured to fit into the bottom longitudinal slot of the housing; a laterally-extending expanded rear portion configured to stop forward movement of the sleeve by impingement upon the rear of the housing; and an opposed pair of gripper or impingement surfaces, at least one of the gripper or impingement surfaces moving interiorly in combination with downward defecting movement of the projection at the top front of the sleeve upon impingement of the projection with the decline toward the rear of the slot and upward deflecting movement of the projection upon impingement of the projection with the incline toward the front of the slot.

An introducer tip is affixed to the housing at the front; the introducer tip having a tip front and a tip rear; and the tip having at least one transverse slit in the tip front to permit egress of an inserted catheter.

In one aspect of the invention, the tip will have at least two transverse slits in the tip spaced apart at approximately 90°.

The deflectable projection at the front of the sleeve is often a peripherally raised region.

The incline for upward deflection is between 1° and 60° inclusive (for some applications, the incline may be more limited, e.g., between 5° and 30° inclusive; and the decline for downward deflection is between 1° and 60° inclusive (once again, for some applications, the decline may be more limited, e.g., between 5° and 30° inclusive.

The advancing mechanism may have an opposed pair of laterally-extending wings.

The introducing tip will preferably have at least two transverse slits, typically spaced apart at 90°.

The degree of incline and the degree of decline may be the same or different. The front introducer tip front may be selected from the group consisting of radiused or cone-shaped.

In one aspect of the invention, the opposed pair of gripper surfaces are essentially semi-circular.

In another aspect of the invention, a catheter insertion kit is described which includes: (1) a catheter; (2) a collection bag; (3) a catheter insertion device, comprising: a substantially hollow cylindrical housing defining a longitudinally extending peripheral slot on one side of the housing; the housing defining an opposed longitudinally extending groove opposed from the peripheral slot; a forward-projecting cylinder extension in communication with the substantially hollow housing; and a means for preventing or retarding rearward motion of the catheter; (5) an advancing mechanism insertable into the cylindrical housing comprising: a split front pair of opposed surfaces, at least one of which moves inwardly in response to impingement of the sleeve with a declining ramp in the housing adjacent the slot and moves outwardly in response to impingement of the sleeve with an inclining ramp in the housing adjacent the slot; the advancing sleeve having a bottom rail which slidingly engages the longitudinally extending groove in the housing; the advancing sleeve having an expanded rear portion; (6) an introducer tip having a front and a rear; the rear of the introducer tip matingly engaging with the forward-projecting cylinder extension of the housing; the front of the tip having at least one transversely extending slit; (7) a front protective cap positioned over at least a portion of the introducer tip; and (8) a rear protective cap positioned over the expanded rear portion of the advancing sleeve.

The collection bag of the kit is sealed exteriorly about at least a portion of a front circumferential periphery of the housing and an interior periphery of the expanded rear portion of the advancing sleeve. The collection bag is accordioned rearward of the front circumferential periphery of the housing is substantially contained within a cavity formed between the expanded rear portion and the rear protective cap. The catheter is positioned within the advancing sleeve and at least a portion is coiled within the expanded rear portion.

The slope for the inclining ramp for upward deflection is between 1° and 60° inclusive and the slope for the declining ramp for downward deflection is between 1° and 60° inclusive, although this range may be narrowed for both slopes between 5° and 30° inclusive. The slope for the inclining ramp and the declining ramp may be the same or different. The split front pair of opposed surfaces are essentially semi-circular.

To the accomplishment of the foregoing and related ends the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

DETAILED DESCRIPTION OF THE INVENTION

Figure 1:
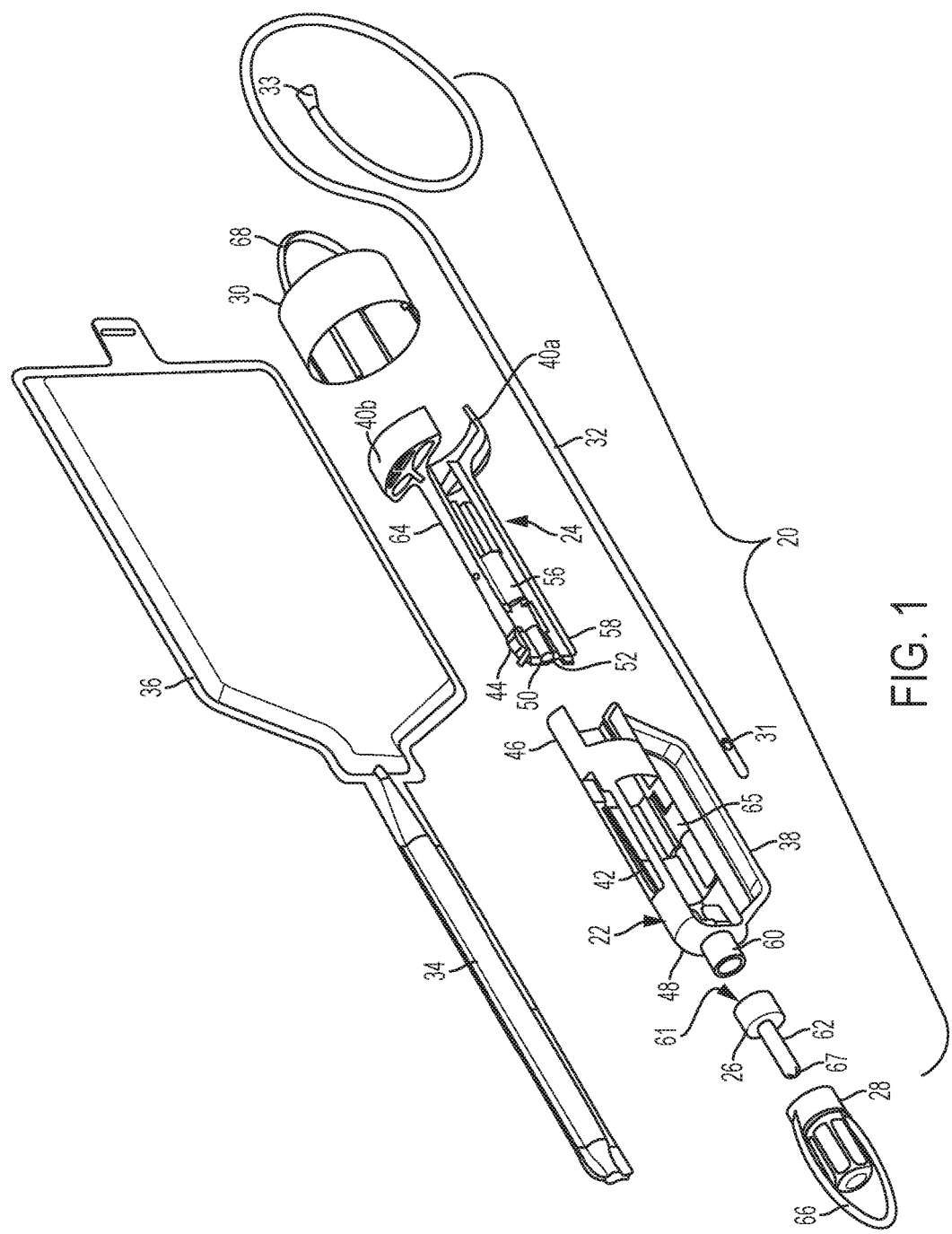
FIG. 1 is an assembly view in perspective of the component parts of the catheter insertion device.

The present systems and apparatuses and methods are understood more readily by reference to the following detailed description, examples, drawing, and claims, and their previous and following description. However, before the present devices, systems, and/or methods are disclosed and described, it is to be understood that this invention is not limited to the specific devices, systems, and/or methods disclosed unless otherwise specified, as such can, of course, vary. It is also to be understood that the terminology used herein is for describing particular aspects only and is not intended to be limiting.

The following description of the invention is provided as an enabling teaching of the invention. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a" component can include two or more such components unless the context indicates otherwise. Also, the words "proximal" and "distal" are used to describe items or portions of items that are situated closer to and away from, respectively, a user or operator such as a surgeon. Thus, for example, the tip or free end of a device may be referred to as the distal end, whereas the generally opposing end or handle may be referred to as the proximal end.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Unless the context clearly indicates otherwise: the word "and" indicates the conjunctive; the word "or" indicates the disjunctive; when the article is phrased in the disjunctive, followed by the words "or both" or "combinations thereof" both the conjunctive and disjunctive are intended.

As used in this application, the term "approximately" is within 10% of the stated value, except where noted.

As used in this application, the term "catheter" includes straight and coude tip catheters wherein the coude varieties include tiemann tip, tapered tip, and olive tip. Also included are catheters which are pre-lubricated as well as those made from hydrophilic polymers.

As used in this application, the terms "proximal" or "proximate" or "front" refer to locations on the device which is closest to the user when the device is in use, while the terms "distal" or "rear" refer to the location on the device which is farther away from the user during use.

Figure 2:
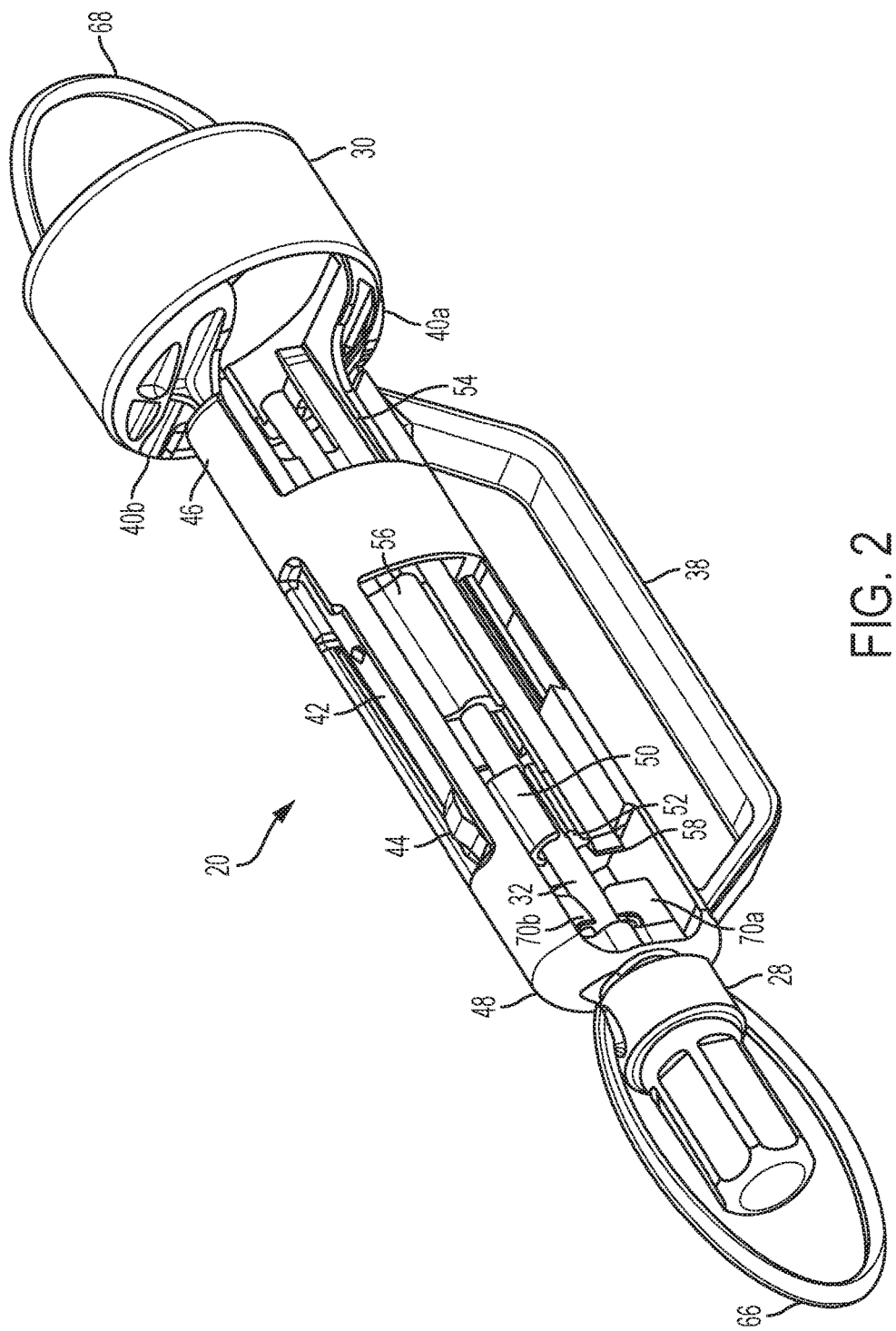
FIG. 2 is a perspective view of the device as assembled with catheter bag and catheter sleeve removed, but illustrating a portion of a catheter positioned within the device.

In one aspect, as illustrated in FIGS. 1-2, the component parts of catheter insertion device 20 include: sleeve housing 22, advancing mechanism 24, introducer tip 26, proximal front cap 28, distal rear cap 30, catheter 32 (not drawn to scale) having at least one proximal opening 31 and at least one distal opening 33, catheter bag sleeve 34, and catheter collection bag 36. The device may be used collectively as a kit or as a subassembly or as individual component parts.

In an exemplified aspect, sleeve housing 22 is essentially hollow having a sleeve housing front proximal segment 48 and a sleeve housing rear distal segment 46. At the proximal end of front sleeve housing proximal segment 48 is male housing circular projection 60 which matingly engages with the rear cylindrical opening 61 of introducer tip 26. Sleeve housing 22 has an optional handle 38 protruding peripherally from the housing on one side and an opposed longitudinal sleeve housing slot 42, the details of which are described in more detail below.

Advancing mechanism 24 is insertable into sleeve housing 22 via sleeve housing rear distal segment 46. Advancing mechanism 24 is operatively configured to reciprocate within sleeve housing 22 in a back-and-forth motion along the longitudinal axis of sleeve housing 22 to advance catheters 32 (of varying lengths, sizes and compositions as is known-in-the-art and within the realm of sound engineering judgment) in a manner to be described more fully below. Briefly, top rail 64 will move longitudinally within sleeve housing 22 as confined within or adjacent sleeve housing slot 42 as well as bottom rail 58 which will move similarly within bottom slot 65. At the front proximal end of top rail 64 is laterally and peripherally-extending projection 44 to assist in maintaining advancing mechanism 24 within longitudinal slot 42 during reciprocating back-and-forth longitudinal movement of advancing mechanism 24. Advancing mechanism 24 has a pair of opposed expanded distal rear sections 40a, 40b which limit the forward direction of advancing mechanism 24 within sleeve housing 22 by contacting engagement with rear distal segment 46 of the mechanism. Opposed expanded rear sections are interconnected by catheter tubing guide sleeve 56 at a position between the front and back sections of the mechanism. Toward the front or distal end of advancing mechanism 24 is a second catheter tubing guide which is split into two segments 50, 52, (preferably semicircular although other shapes are envisioned and within the scope of this invention. Alternative shapes to an inverted semicircular shape as illustrated in cross-section, would include various shapes in cross-section, better illustrated in FIGS. 19A-19D. At least one of segments 50, 52 is transversely movable to the longitudinal axis of advancing mechanism 24.

As illustrated at least in FIGS. 1-2, rear cylindrical opening 61 of introducer tip 26 is matingly engaged with male circular projection 60 positioned at the front of housing 22. The mating engagement may be frictional engagement, or may be more permanent (e.g., adhesively secured using a permanent, non-permanent or removable adhesive) as end-use applications may demand. At the front of introducer tip is hollow rod-like insertion projection 62 for which at its forward-most location is at least one transverse slit, preferably two or more transverse slits 67 which permit egress of catheter 32, yet also may retard rearward movement of the catheter during operation. When two transverse slits are employed, the slits are generally positioned at 90° from each other. For larger numbers of transverse slits, the preferred geometry is to employ an equal amount of spacing between the circumference of the slits, i.e., 360°/n slit segments, a slit segment defined as a slit which originates at a circumference and terminates at the apex of the introducer tip. The shape of the introducer tip may vary in accord with end-user needs and may be radiused or cone-shaped, or any other geometric shape within sound engineering judgment.

In yet another aspect, front cap 28 is frictionally affixed to tip introducer 26. The cap may optionally have a loop 66 to assist the user of the device in removing the cap. In operation, this cap is removed prior to beginning insertion of the catheter into a user's urethra. Similarly, rear cap 30 is frictionally affixed to the pair of opposed expanded rear sections 40a, 40b, optionally with a loop 68 to assist the user of the device in effecting reciprocating movement.

Figure 6:
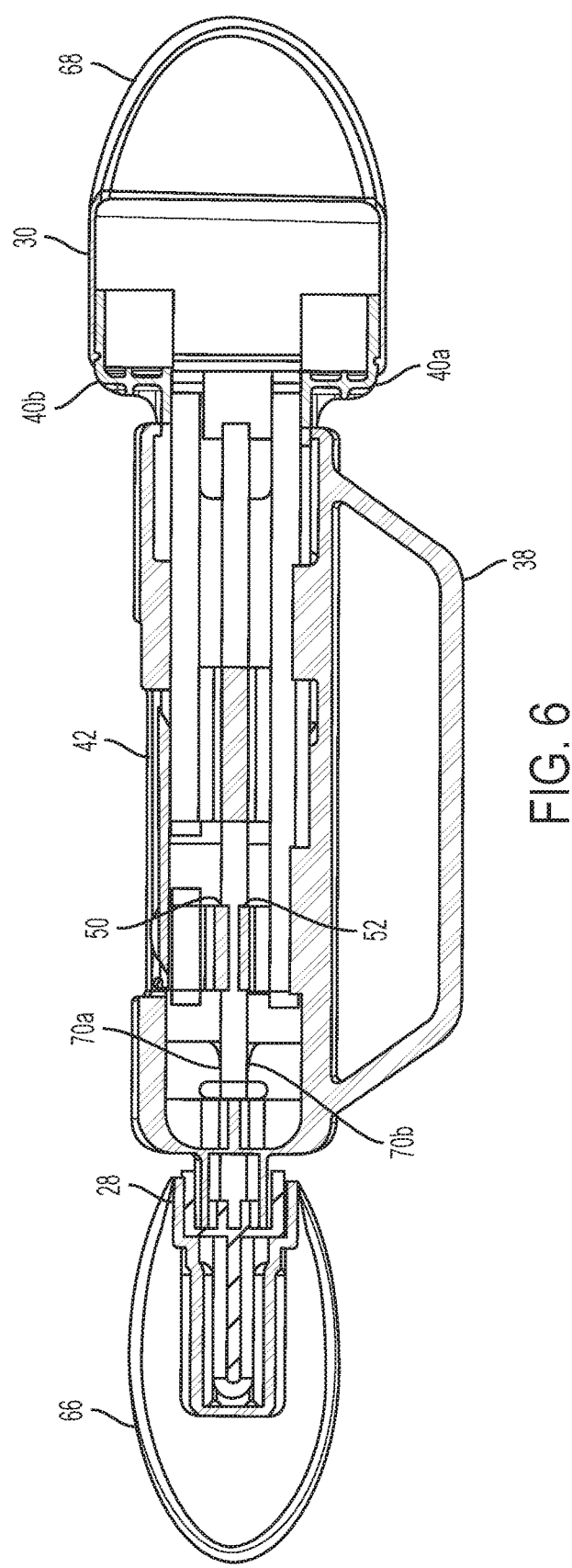
FIG. 6 is a cross-sectional side view of the device illustrating the advancement mechanism in its first or proximal position with portions of the catheter sleeve removed for purposes of clarity.
Figure 14:
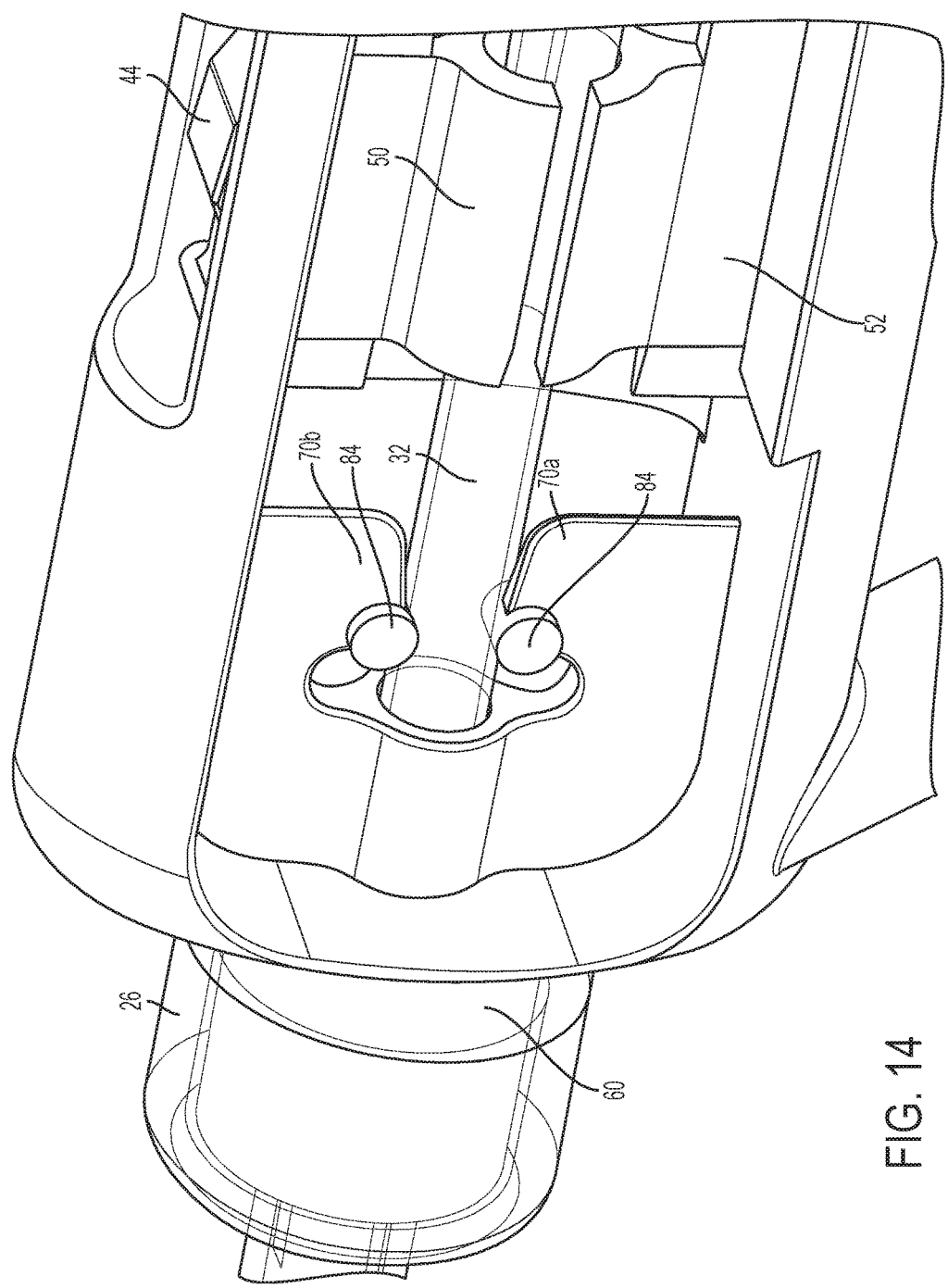
FIG. 14 is an enlarged side elevational view in partial cross-section illustrating one alternative for a rearward retarding mechanism for the catheter.

As better illustrated in FIGS. 2 & 6, in one embodiment, sleeve housing 22 has at least one pair of opposed impingement surfaces or synonymously gripper jaws 70a, 70b a gap between the jaws or impingement surfaces being dimensioned to be slightly less than the outer diameter of catheter 32 yet still permitting frictional forward movement of the catheter. The opposed jaws retard and often prevent, rearward movement of catheter 32 when advancing sleeve mechanism 24 is being retracted to its rearward second or distal position. The interior surface of the jaws may be straight or curved, and optionally contains a friction-enhancing mechanism, such as a roughened surface or striations to assist in preventing the catheter tube from reversing direction. While a simple friction mechanism is shown, other mechanisms are possible, and would include for example, a rachet and pawl arrangement or a unidirectional roller or pair of rollers. As better illustrated in FIG. 14, the opposed mechanism may be a pair of circular surfaces 84, shown as non-pivoting in the figure, but with the inclusion of a one-way axis, could be made to be unidirectional in rotation. While a pair of circular surfaces is illustrated, other options include any impingement surface which contacts the exterior outer diameter of catheter 32 and slightly compresses it. The amount of compression can range from any amount greater than zero to 50% inclusive, more preferably 0.01 to 25% inclusive, and most preferably 0.1 to 10% inclusive.

Figure 3:
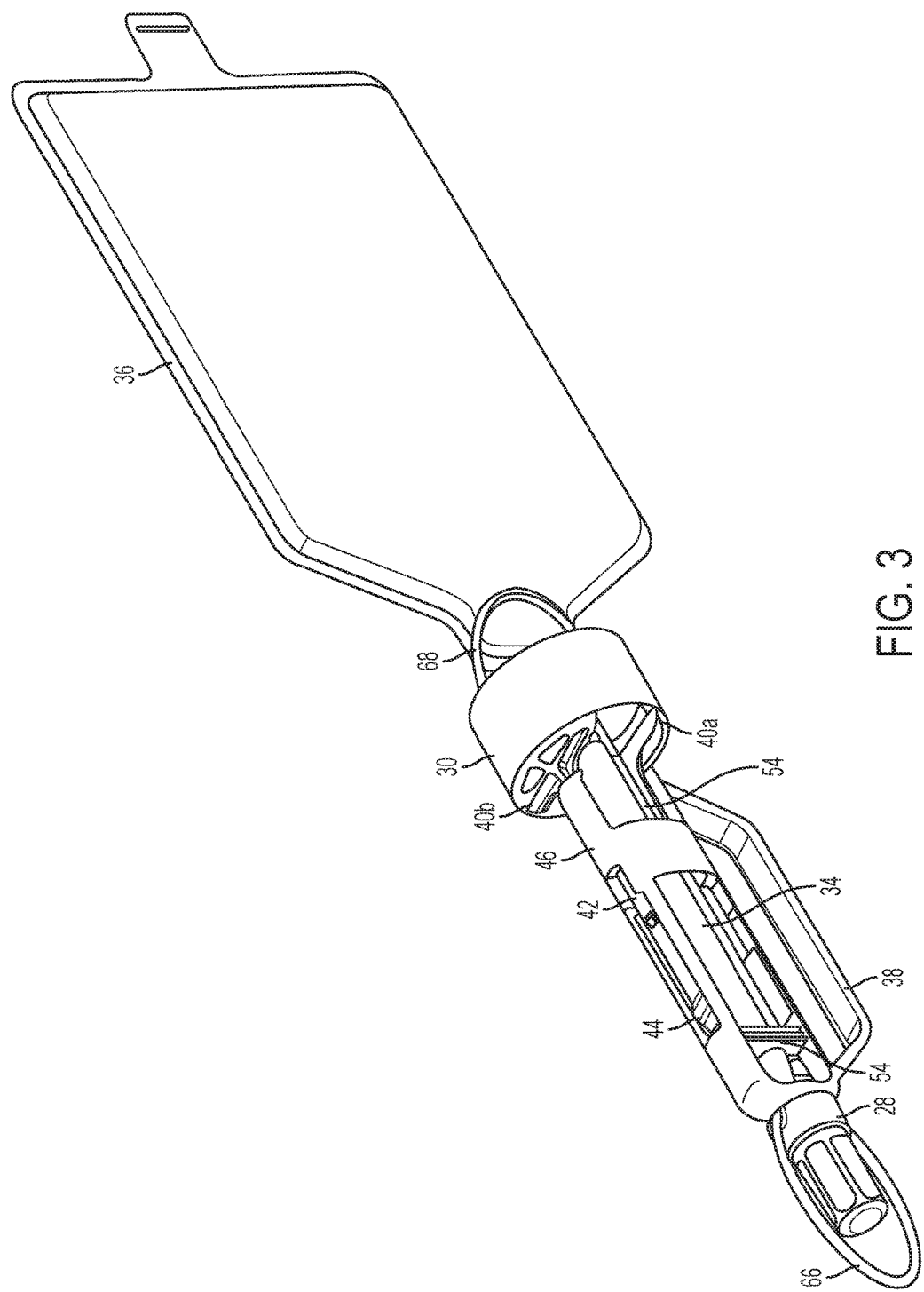
FIG. 3 is a perspective view of the device of FIG. 2 illustrating the catheter sleeve positioned about the catheter in the initial or first or forwardmost position of the advancing mechanism in the housing with associated front and rear end caps affixed as well as illustrating the rearward extending collection bag, the catheter bag sleeve depicted as accordioned toward the proximal end of the device.
Figure 4:
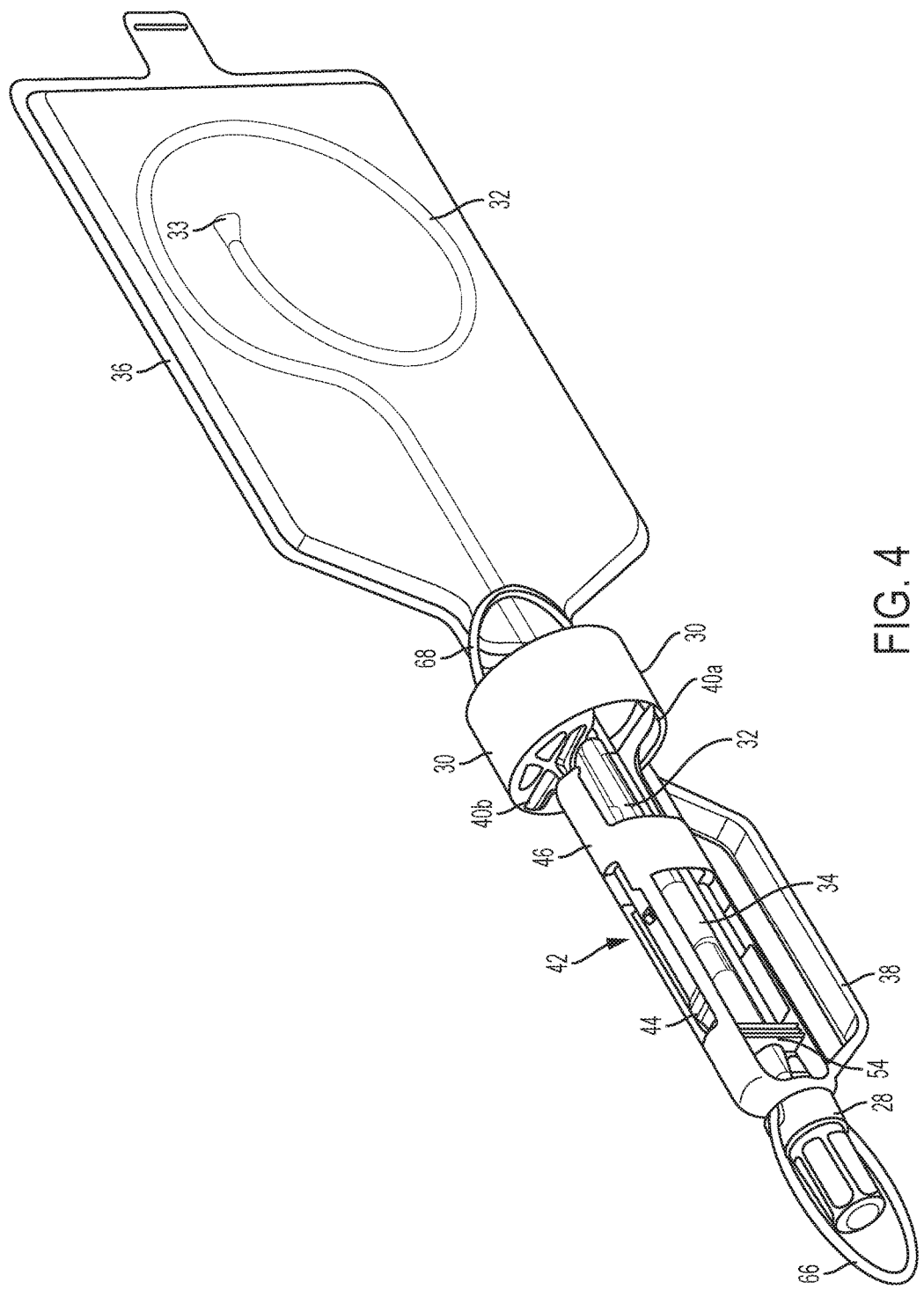
FIG. 4 is a view similar to FIG. 3 with the collection bag and catheter sleeve in partial cut-away illustrating the catheter in a coiled position within the collection bag and the advancement mechanism in its initial or first or forwardmost position.
Figure 5:
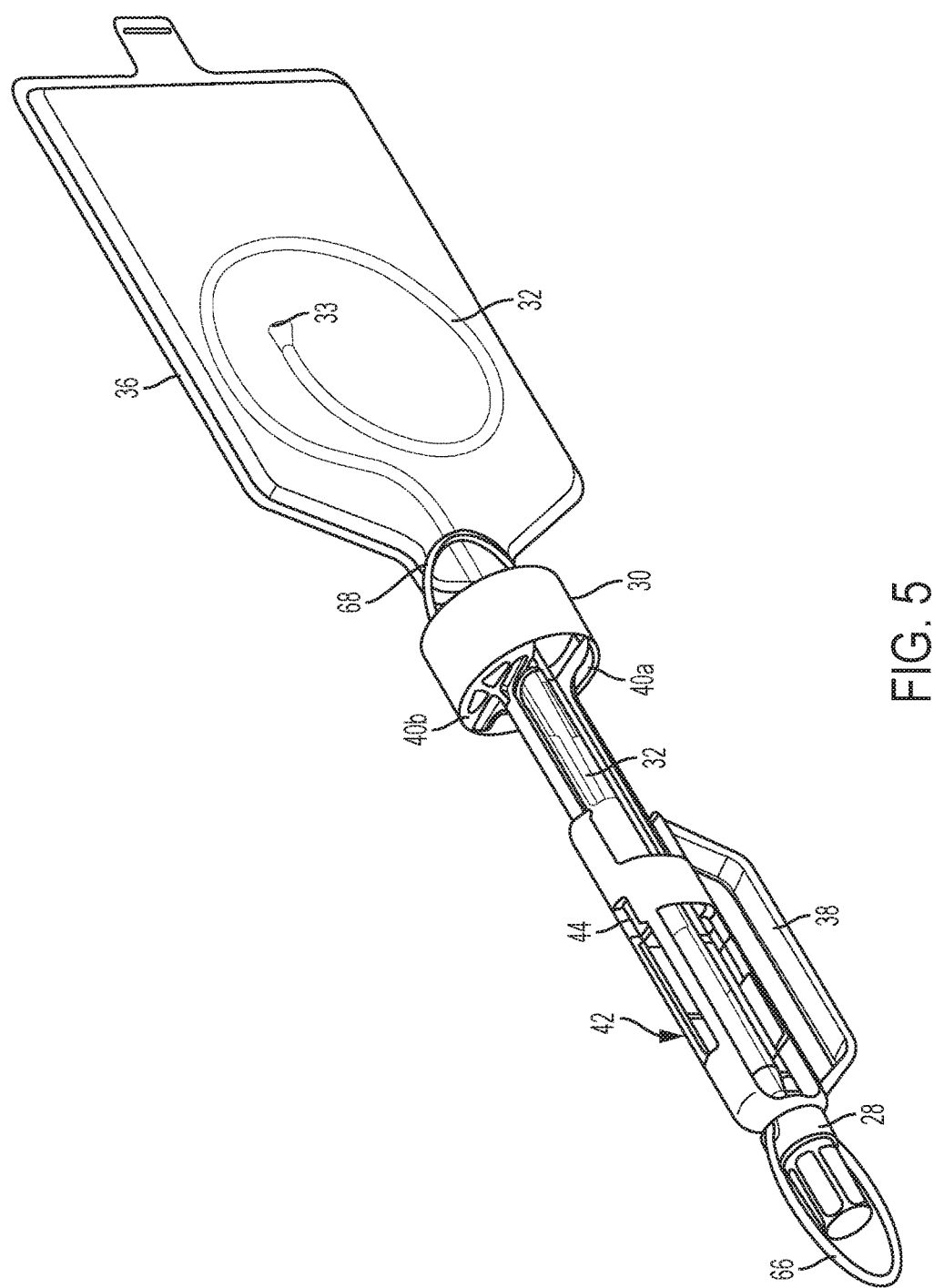
FIG. 5 is a view similar to FIG. 4 illustrating the advancement mechanism in its rearward or second position, illustrating the previously shown accordion-like folds of the catheter sleeve in their expanded form.

In its assembled state as received by a user, distal end 33 of catheter 32 has been inserted into the proximal end of catheter bag sleeve 34 and threaded through catheter bag sleeve 34 and into collection bag 36 as illustrated in FIG. 4. The proximal end of catheter bag sleeve 34 is positioned within advancement mechanism 24 which is positioned within housing 22, at least a portion of the proximal end of the catheter bag sleeve is accordioned 54 (see at least FIGS. 3 & 4) toward the proximal end of the housing when peripherally-extending projection 44 is in its first or proximal position. When peripherally-extending projection 44 is in its rearward or second position, catheter bag sleeve flattens the accordion design as illustrated in FIG. 5.

Figure 7:
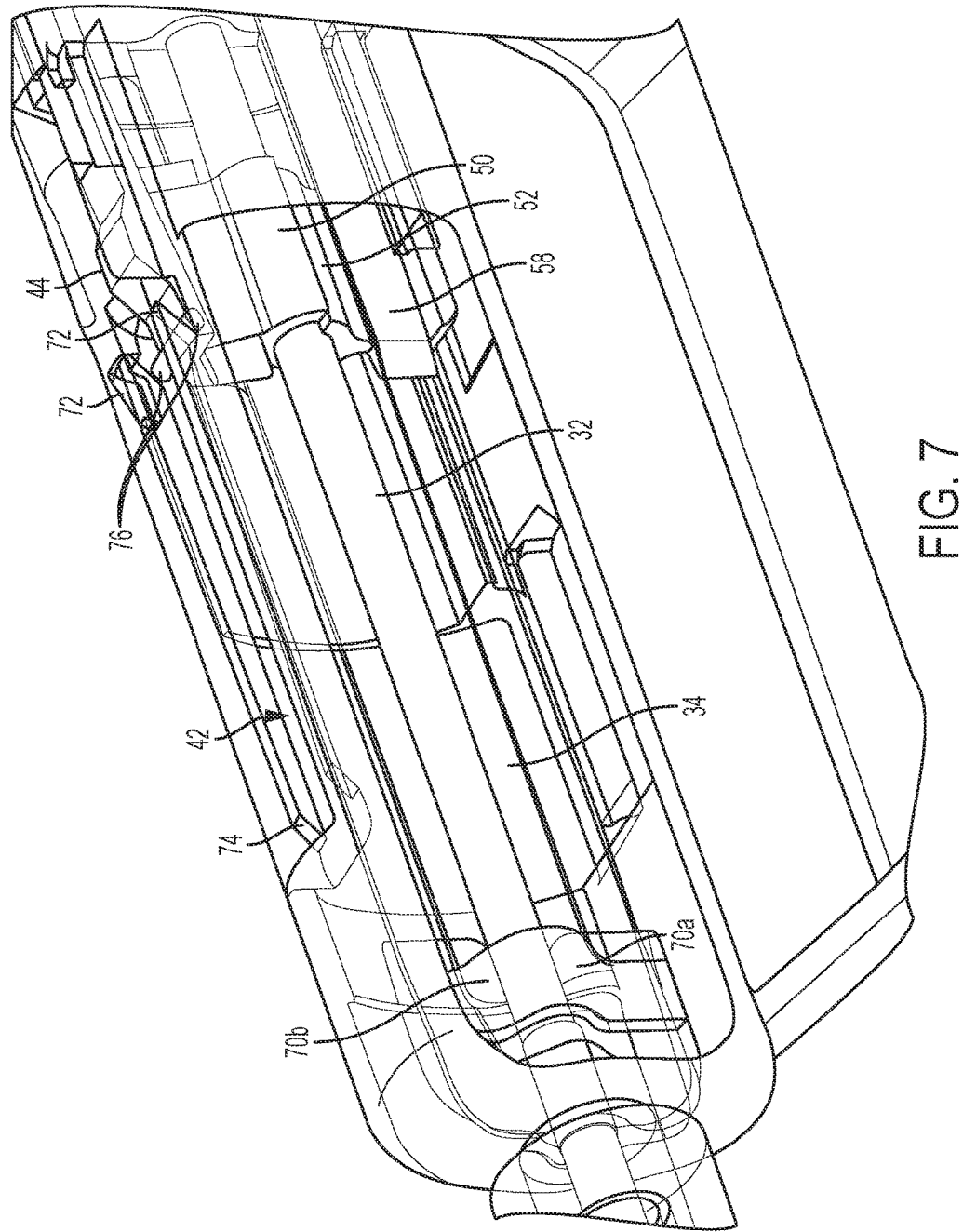
FIG. 7 is an exploded perspective view of the advancement mechanism with catheter sleeve removed when in its second rearward position with the advancement mechanism making initial engagement with the catheter by impingement with a declined ramp in the device housing.
Figure 17:
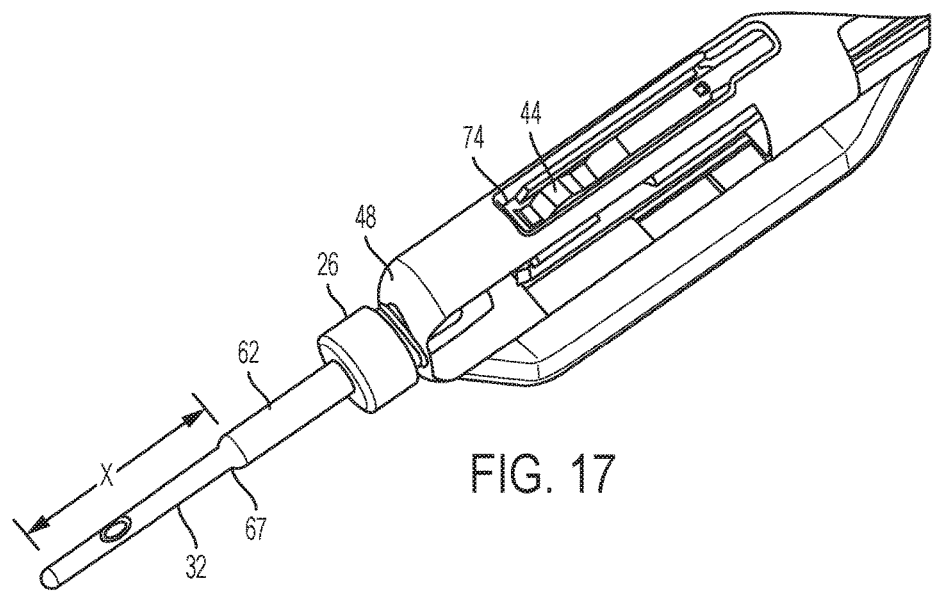
FIG. 17 is a top perspective view similar to FIG. 15 illustrating the advancement mechanism in its first or proximal position, the catheter extending beyond the tip of front cap rod-like tip for a distance "x"
Figure 18:
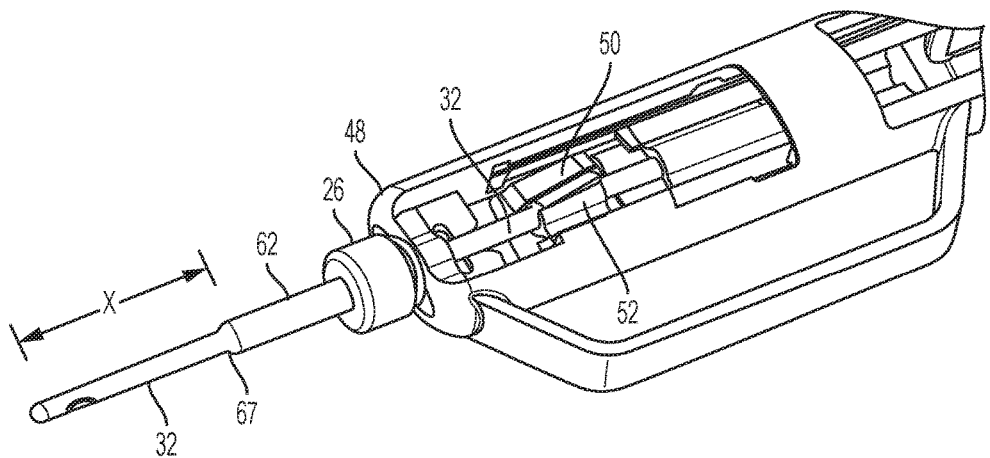
FIG. 18 is a side perspective view similar to FIG. 17 illustrating the advancement mechanism in its first or proximal position beginning its impingement on the incline ramp for at least partial disengagement with the catheter.
Figure 19A:
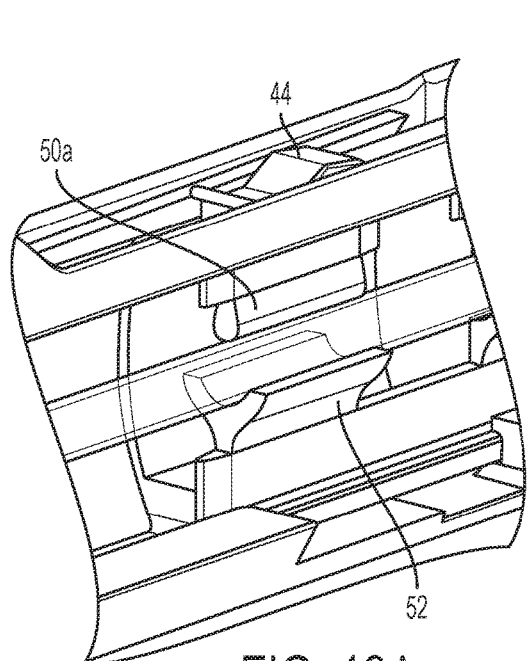
FIG. 19A is a perspective view illustrating a circular shape in cross-section as an alternative to inverted semicircular shape of upper catheter tubing guide segment 50.
Figure 19B:
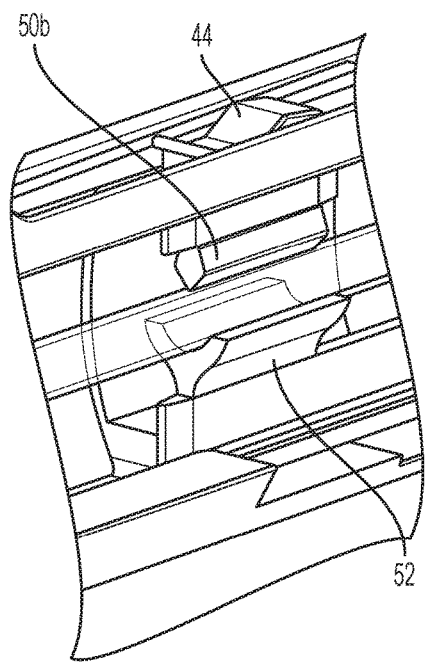
FIG. 19B is a perspective view illustrating a square or diamond-shape in cross-section as an alternative to the inverted semicircular shape of upper catheter tubing guide segment 50.
Figure 19C:
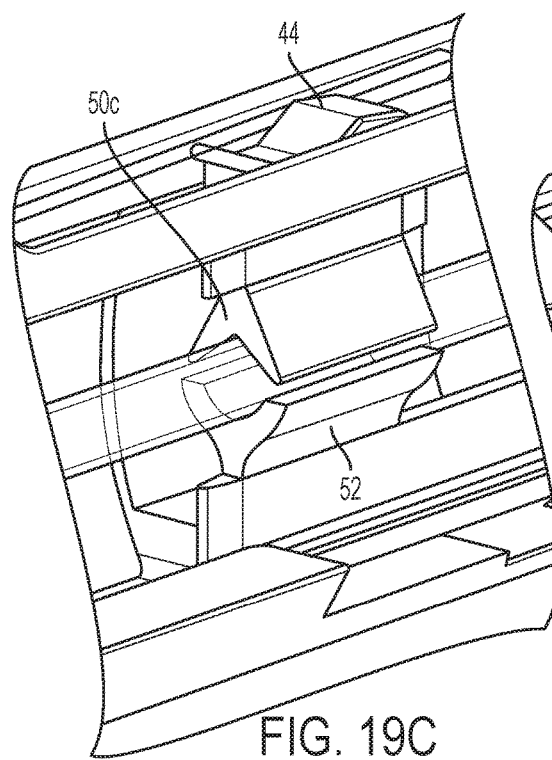
FIG. 19C is a perspective view illustrating an grooved triangle or quadrilateral shape in cross-section as an alternative to the inverted semicircular shape of upper catheter tubing guide segment 50.
Figure 19D:
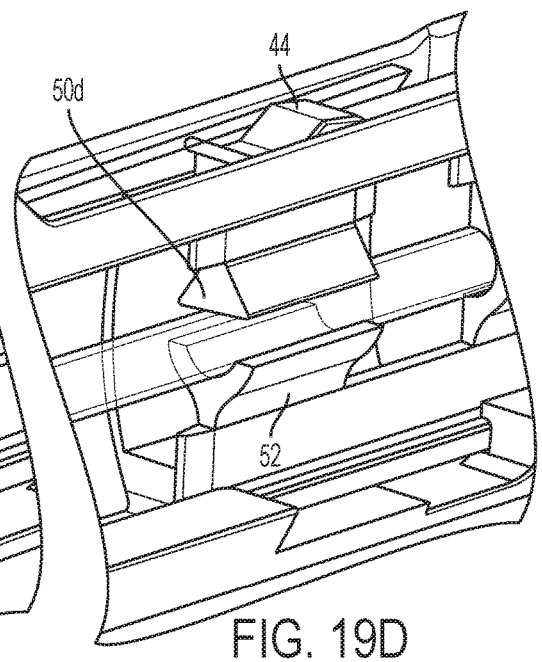
FIG. 19D is a perspective view illustrating a quadrilateral or triangle shape in cross-section as an alternative to the inverted semicircular shape of upper catheter tubing guide segment 50.

FIGS. 7-10 illustrate the use of the reciprocating advancement movement. FIG. 7 illustrates the device with the advancement mechanism in the second or distal position. Peripherally-extending projection 44 is positioned at the rear of sleeve housing 22 and at the rear of longitudinal slot 42. In this position, transverse projections 76 make contacting engagement with decline ramps 72 and at least one of the catheter tubing guide segments (guide segment 50 in the figure) is depressed into contacting engagement with catheter 32 and at least a portion of lower catheter tubing guide segment 52. In the illustration, upper catheter tubing guide segment 50 is shown contacting the catheter at an angle between 1° and 60° inclusive, although both larger and smaller declination angles are within the scope of the invention as determined by sound engineering judgment. The angle of declination as well as the length of decline ramp 72 is determined at least in part, by the amount of compressive force desired by the manufacturer and end-user to facilitate forward movement of catheter 32. Contacting frictional and compressive engagement of upper and lower catheter tubing guide segments 50, 52, are used to advance catheter 32. Catheter advancement is effected by pushing the distal end of advancing mechanism 24 distal end caps 40a, 40b, inside distal end cap 30, the distance traveled by catheter 32 being essentially the same as the length of longitudinal slot 42 and illustrated by distance "X" in FIGS. 17-18.

Figure 8:
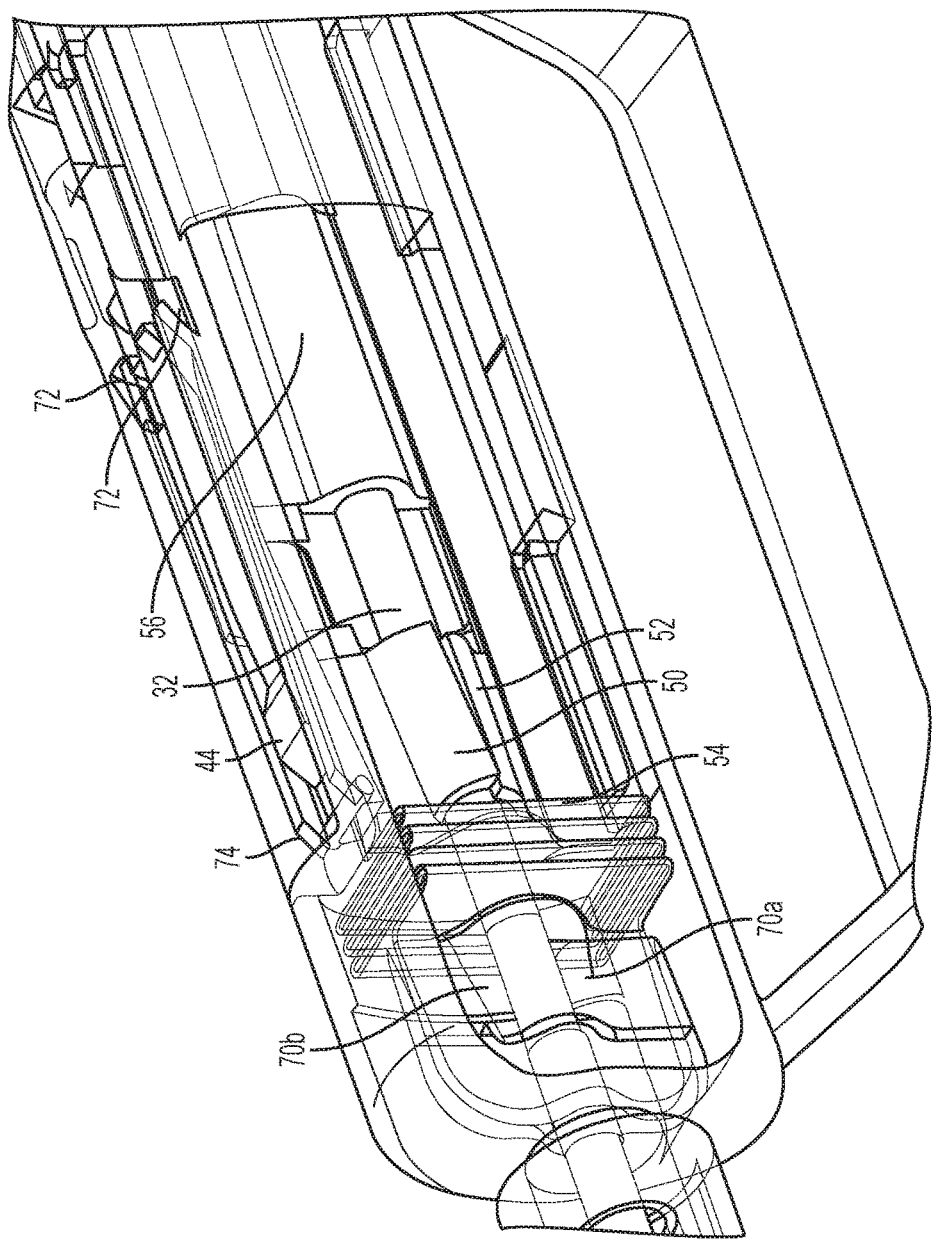
FIG. 8 is an exploded view of the advancement mechanism with catheter sleeve partially removed and the mechanism is in its first position with the advancement mechanism about to release the catheter.
Figure 9:
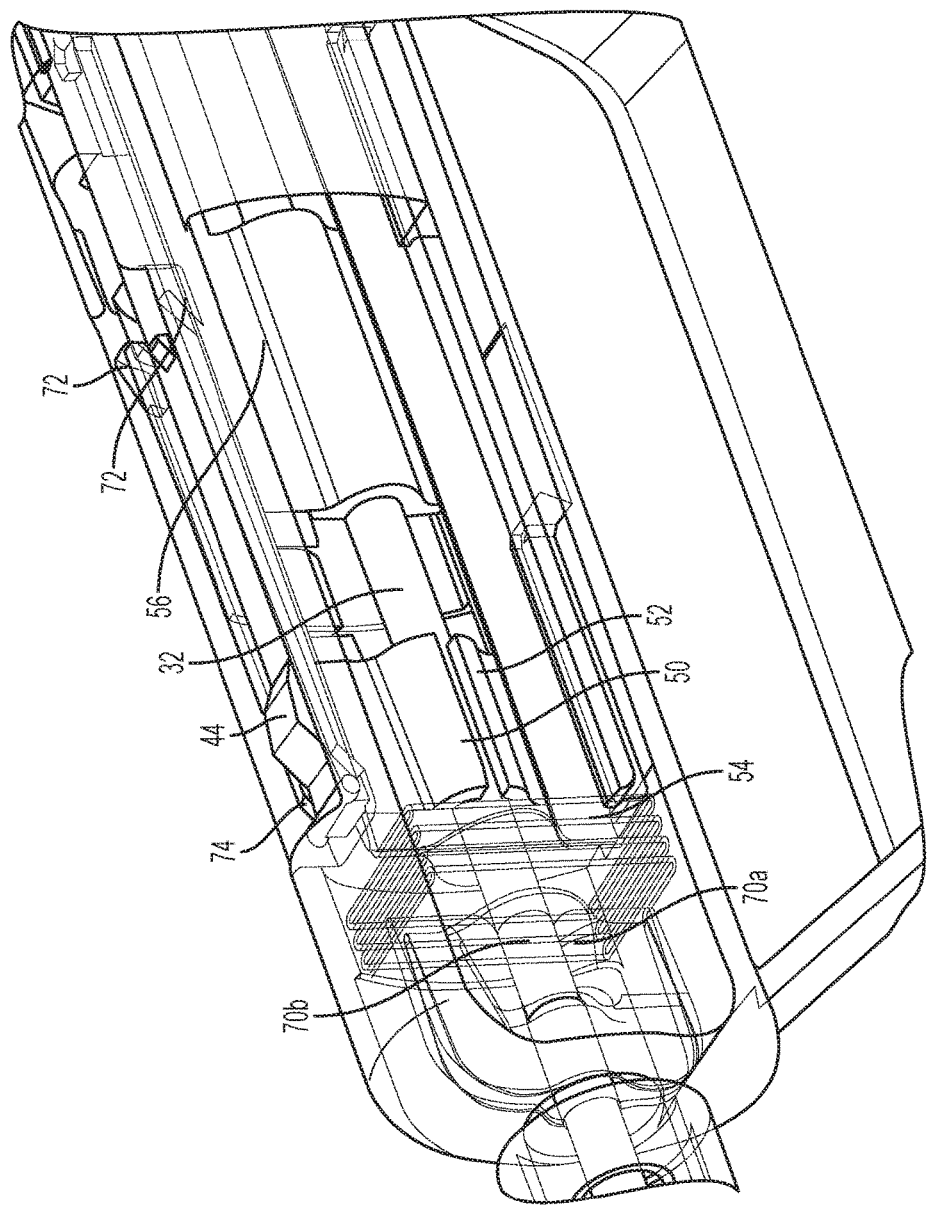
FIG. 9 is an exploded view similar to FIG. 8 with the advancement mechanism released from the periphery of the catheter.
Figure 10:
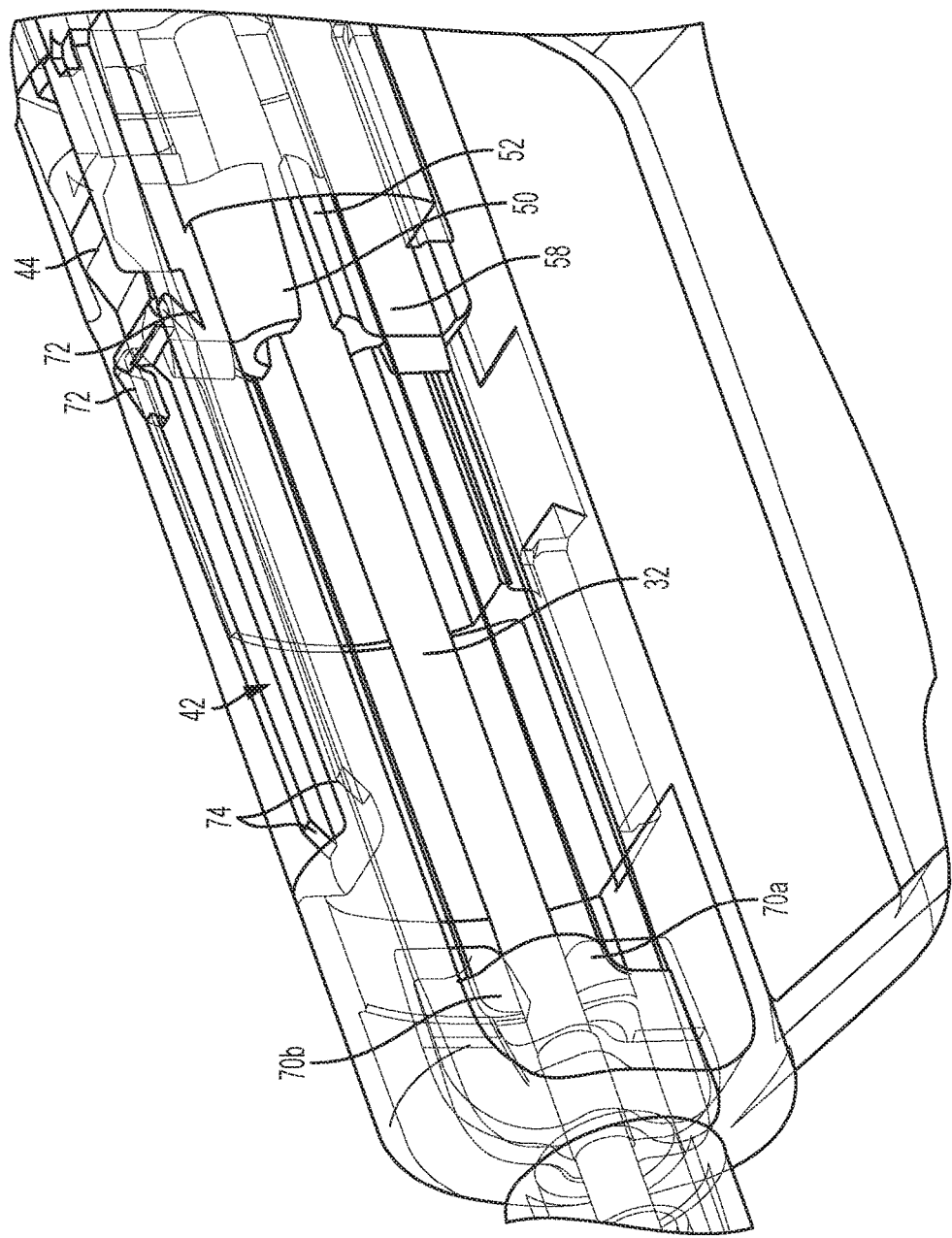
FIG. 10 is an exploded view similar to FIG. 8 with the advancement mechanism approaching its second rearward position.
Figure 11:
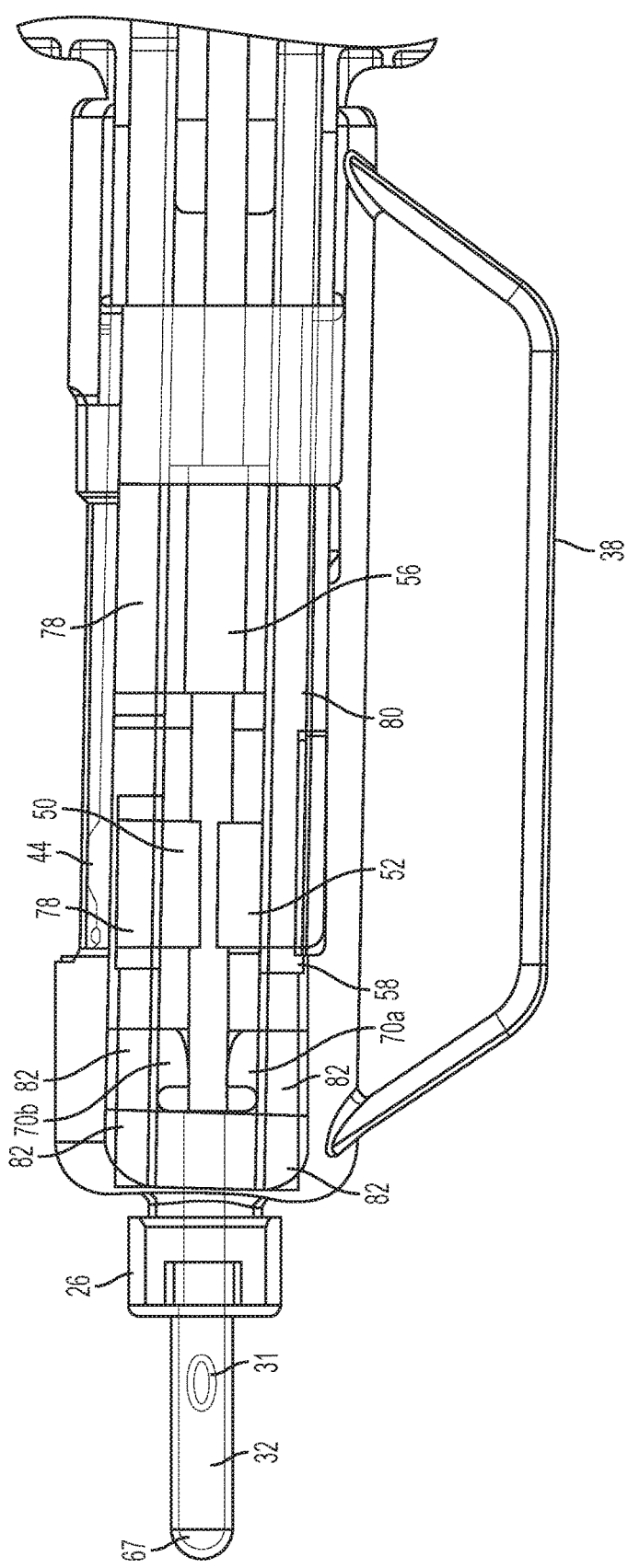
FIG. 11 is a partial side elevational view with catheter bag and catheter bag sleeve removed, but illustrating the catheter positioned within the proximal end cap.

FIG. 8 illustrates the advancement of catheter 32 upon forward longitudinal movement of advancement mechanism 24 to a location just prior to completion of the forward movement within longitudinal slot 42. It is noted that upon initial contact with decline ramp 72, the distal end of upper catheter tubing guide segment 50 of advancement mechanism 24 is deflected downward to increase the contacting force with catheter 32. This increased pressure is maintained for the duration of the forward movement within longitudinal slot 42 and the catheter is advanced by approximately the length of the slot or the distance "X" in FIGS. 17-18. During this forward movement, catheter bag sleeve 34 is accordioned toward the front of advancing mechanism 24 within sleeve housing 22 (see accordion-like folds 54). Upon projection 44 reaching the forward terminus of slot 42, transverse projections 76 of peripherally extending projection 50, which are resiliently biased to maintain their original geometry, will move upward, aided by incline ramp 74 (better illustrated in a combination of FIGS. 8-9. The separation of split upper and lower tubing guide segments 50, 52 permits retraction of projection 44 to its rearward distal position without correspondingly retracting the catheter, aided by the frictional engagement of jaws 70a, 70b, hindering rearward movement of the catheter tubing, in combination of the at least one transverse slit 67 of the hollow rod-like insertion projection 62 of introducer tip 26. Upon peripherally extending projection 44 reaching the rear of longitudinal slot 42, transverse projections 76 may optionally be extended upwardly for ultimate downward motion as illustrated in FIG. 7.

The angle for upward deflection of incline ramp 74 is between 1° and 60° inclusive; and the decline angle for downward deflection of decline ramp 76 is between 1° and 60° inclusive. The deflectable projection has an opposed pair of laterally-extending wings or transverse projections 76. In another embodiment, the incline ramp of the device is more preferably between 5° and 30° inclusive, and the decline for downward deflection is between 5° and 30° inclusive. It should be noted that the slope and/or angles of the incline and decline ramps may be the same or different.

Figure 12:
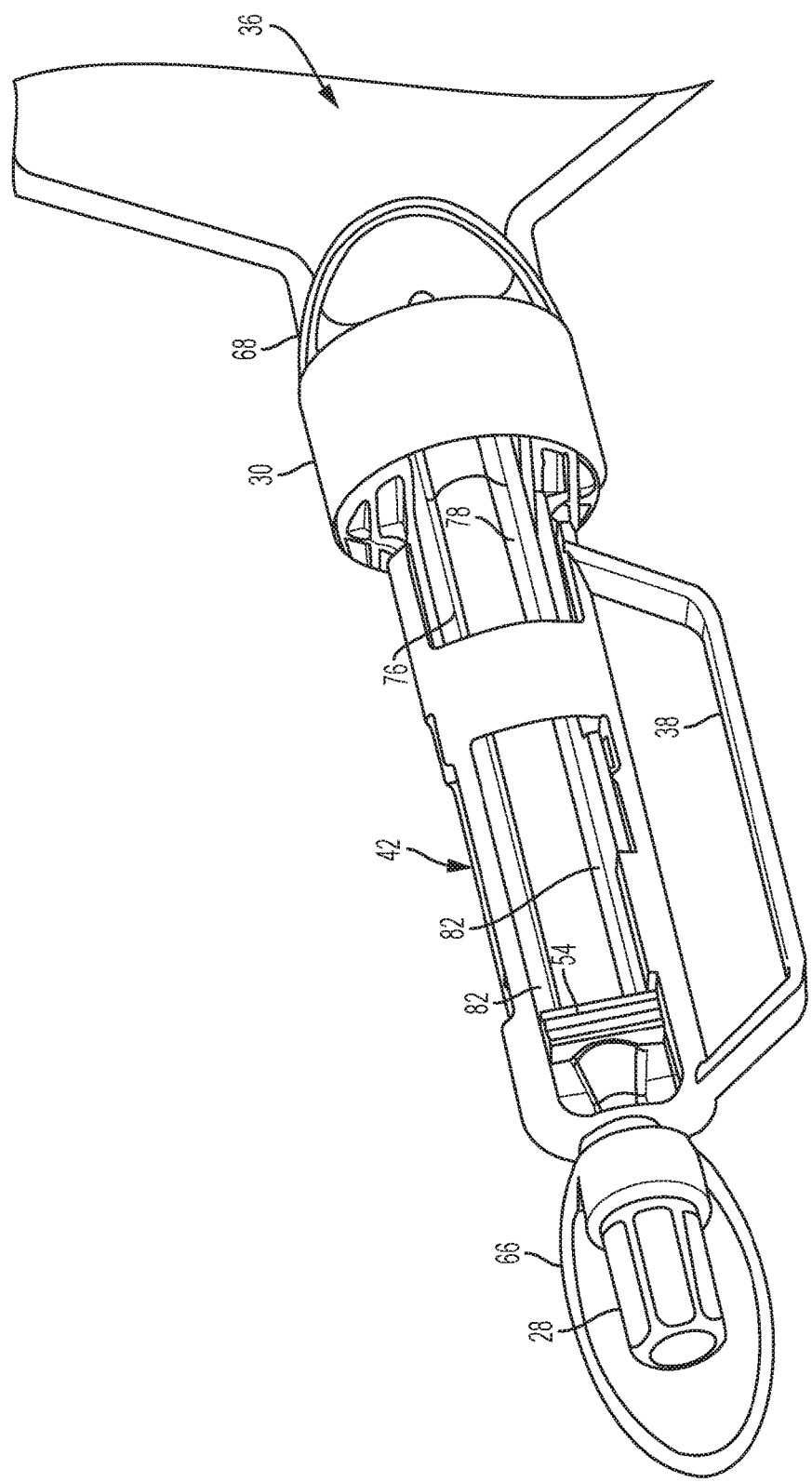
FIG. 12 is a partial enlarged perspective view of the accordioned catheter sleeve within the device but with the advancing mechanism not shown, the device in the proximal or first position, the catheter bag only partially shown.
Figure 13:
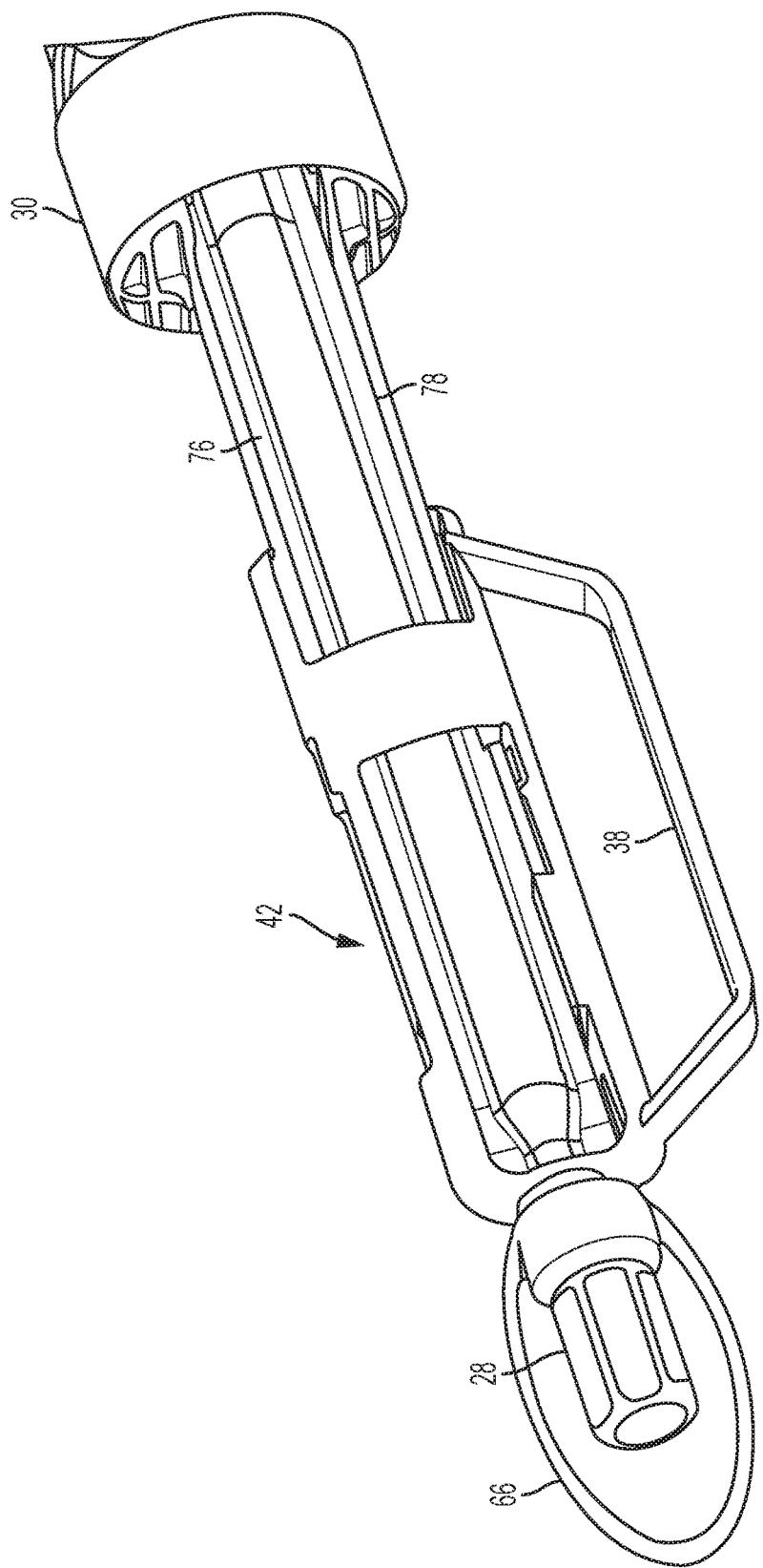
FIG. 13 is an enlarged perspective view of FIG. 12 with the device in the distal or second position.

It should be noted that to maintain the sterility of catheter 32, catheter bag sleeve 34 is sealed exteriorly about at least a portion of a front circumferential periphery of sleeve housing 22 and also sealed exteriorly about at least a portion of the top and bottom rails of advancing mechanism 24. The collection sleeve is compressed in an accordioned manner 54 about the front circumferential periphery of sleeve housing 22 when the advancing mechanism is in its proximal or first location within longitudinal slot 42 and is in its non-accordioned state when the advancing mechanism is in its distal location within longitudinal slot. Catheter bag sleeve 34 is typically heat sealed to itself on opposed sides 80, as illustrated in FIGS. 12-13. It is also adhered to a proximal portion 82 of sleeve housing 22 and to at least a portion 78 of top rail 64 and at least a portion 80 of bottom rail 58. It is this fixed connection that upon reciprocating movement of advancing mechanism 24 will accordion the sleeve when the advancing mechanism movement is toward the proximal end or first position (shown in FIG. 12) and will remove the accordion folds of the sleeve when the advancing mechanism movement is toward the distal end or second position (shown in FIG. 13). It should be noted that when the catheter bag sleeve is sealed as described above, the kit is a closed sterile system to the end-user, minimizing infection risks.

Figure 15:
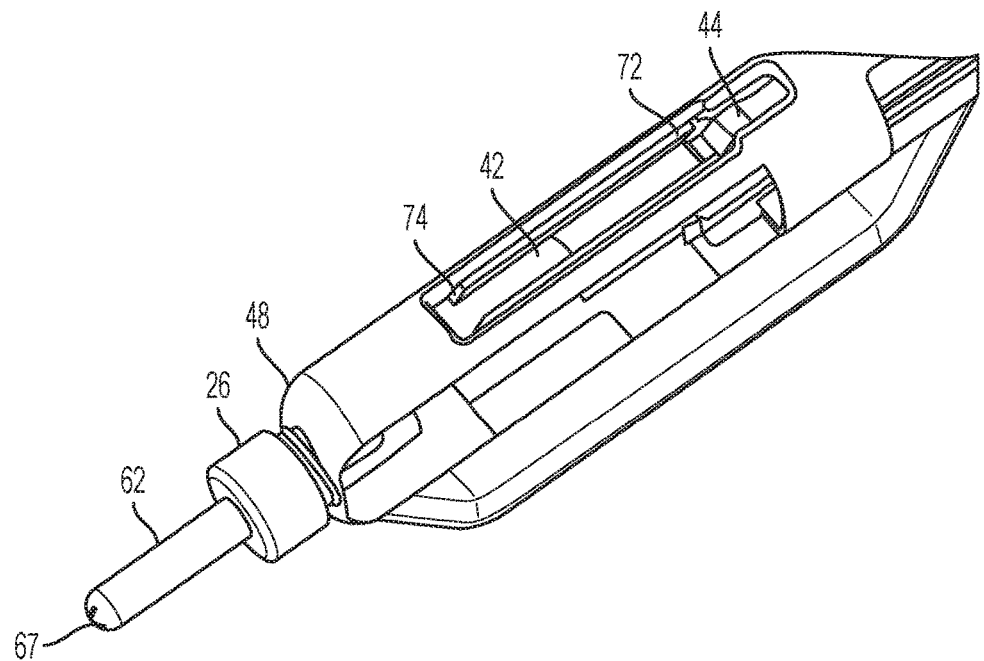
FIG. 15 is a top perspective view of the catheter with the advancement mechanism in its second or distal position.
Figure 16:
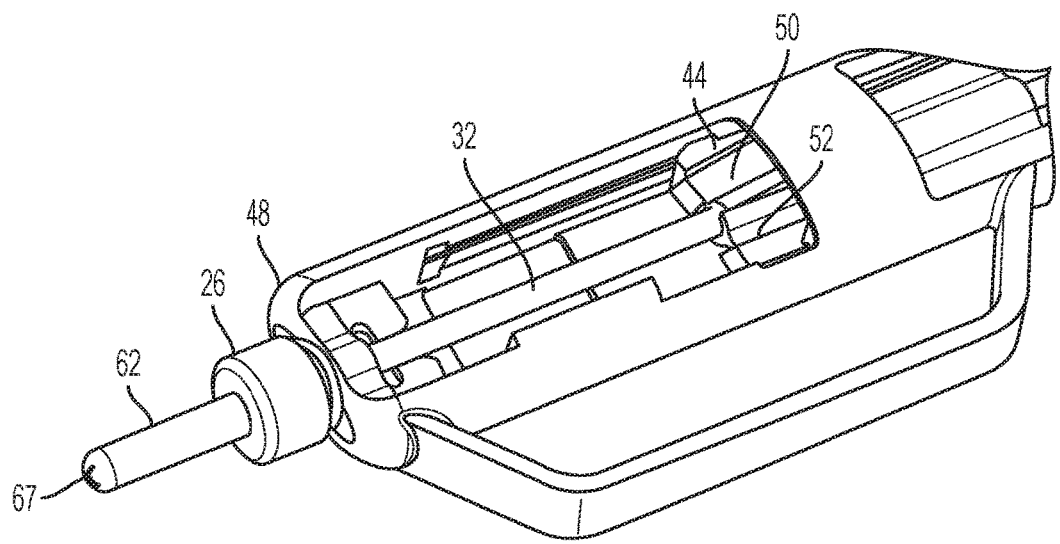
FIG. 16 is a side perspective view of the catheter illustrating the advancement mechanism in its second or distal position beginning its impingement on the decline ramp for at least partial engagement with the catheter.

As shown by a combination of FIGS. 15-16 & FIGS. 17-18, and with advancement mechanism 24 is positioned in its second or distal position shown in FIGS. 15-16, catheter 32 is not protruding from slits 67 of rod-like projection 62 of introducer tip 26. Upon continued proximal movement (better illustrated in FIG. 16), upper catheter tubing guide segment 50 exerts at least a sufficient amount of compressive force in combination with decline ramps 72 to cooperatively move catheter 32 in a forward direction. Upon peripherally extending projection 44 moving toward the proximal end of longitudinal slot 42, catheter cooperatively moves forward by a distance essentially equal to the length of the longitudinal slot, advancing catheter by approximately a distance "X" illustrated in FIGS. 17-18. The user subsequently moves catheter advancement mechanism 24 back toward the position illustrated in FIGS. 16-17 for a second cycle of operation as described above.

A range of polymers may be used for the construction of the insertion device and its component parts, e.g., polyolefins: a non-limiting list including at least, polypropylene, polyethylene, low density polyethylene; polycarbonates; and polyvinyl chloride or PVC (DEHP-free).

A range of polymers are used for the construction of catheters, including silicone rubber, nylon, polyurethane, polyethylene terephthalate (PET), latex, and thermoplastic elastomers. Silicone is one of the most common choices because it is inert and unreactive to body fluids and a range of medical fluids with which it might come into contact.

At least one important polymeric property for all components of the above device, is the ability to maintain structural integrity upon exposure to sterilizing radiation, e.g., gamma-radiation.

There are many different types of catheters for bladder problems. A typical modern intermittent catheter is made from polyurethane and comes in different lengths and sizes for men, women and children. The most advanced catheters have a thin hydrophilic surface coating. When immersed in water this coating swells to a smooth, slippery film making the catheter safer and more comfortable to insert.

In the foregoing description, certain terms have been used for brevity, clearness and understanding; but no unnecessary limitations are to be implied therefrom beyond the requirements of the Prior Art, because such terms are used for descriptive purposes and are intended to be broadly construed. Moreover, the description and illustration of the invention is by way of example, and the scope of the invention is not limited to the exact details shown or described.

The best mode for carrying out the invention has been described for purposes of illustrating the best mode known to the applicant at the time. The examples are illustrative only and not meant to limit the invention, as measured by the scope and merit of the claims. The invention has been described with reference to, preferred and alternate embodiments. Obviously, modifications and alterations will occur to others upon the reading and understanding of the specification. It is intended to include all such modifications and alterations insofar as they come within the scope of the appended claims or the equivalents thereof.

What is claimed is:

1. A catheter insertion device which comprises:
   a substantially hollow housing having a longitudinal axis, the housing having a front and a rear and defining at least one upper longitudinal slot on an exterior of the housing;
   a first ramp positioned toward a rear of the at least one upper longitudinal slot, the first ramp having a decline for downward deflection;
   a second ramp positioned toward a front of the at least one upper longitudinal slot, the first ramp having an incline for upward deflection;
   the housing further defining a bottom longitudinal slot;
   an opposed pair of impingement surfaces toward a front of the housing to assist in preventing rearward movement of an inserted catheter tube;
   an advancement sleeve longitudinally insertable along the longitudinal axis of the housing into at least a portion of the housing from the rear, the advancement sleeve movable in a back-and-forth direction along the longitudinal axis of the housing, the advancement sleeve having a sleeve top, a sleeve bottom, a sleeve front and a sleeve rear; the advancement sleeve comprising:
   an inwardly and outwardly deflectable front top rail portion at the top front of the sleeve, the inward and outward deflection occurring transverse to the longitudinal axis of the advancement sleeve;
   a bottom rail on the advancement sleeve configured to fit into the bottom longitudinal slot of the housing;
   a laterally-extending expanded rear portion configured to stop forward movement of the advancement sleeve by contacting engagement with the rear of the housing;
   and an opposed pair of tubing guides, at least one of the tubing guides moving interiorly in combination with downward defecting movement of the top rail upon impingement of at least a portion of the top rail with the first ramp and upward deflecting movement of the top rail upon impingement of at least a portion of the top rail with the second ramp;
   an introducer tip affixed to the housing at the front;
   the introducer tip having a tip front and a tip rear; and the tip having at least one transverse slit in the tip front to permit egress of an inserted catheter.

2. The device of claim 1 wherein the tip further comprises:
   at least two transverse slits in the tip spaced apart at approximately 90°.

3. The device of claim 1 wherein the deflectable projection at the front of the sleeve is
   a transversely extending projection.

4. The device of claim 1 wherein
   an incline angle for upward deflection is between 1° and 60° inclusive; and
   a decline angle for downward deflection is between 1° and 60° inclusive.

5. The device of claim 1 wherein
   the tip has at least two transverse slits.

6. The device of claim 5 wherein
   the two transverse slits are spaced apart at 90°.

7. The device of claim 4 wherein
   the incline angle for upward deflection is between 5° and 30° inclusive; and
   the decline angle for downward deflection is between 5° and 30° inclusive.

8. The device of claim 1 wherein
   the angle of incline and the angle of decline are different.

9. The device of claim 1 wherein
   the angle of incline and the angle of decline are the same.

10. The device of claim 1 wherein
    the opposed pair of tubing guides are essentially semi-circular.

11. A catheter insertion kit which comprises:
    a collection bag;
    a catheter insertion device, comprising:
       a substantially hollow cylindrical housing defining a longitudinally extending peripheral slot on one side of the housing;
          the housing defining an opposed longitudinally extending groove opposed from the peripheral slot;
          a forward-projecting cylinder extension in communication with the substantially hollow housing; and
          a means for preventing or retarding rearward motion of the catheter;
       an advancing sleeve insertable into the cylindrical housing and having a first proximal position and a second distal position, comprising:
          a split front pair of opposed surfaces, at least one of which moves inwardly in response to impingement of the advancing sleeve with a declining ramp in the housing adjacent the longitudinally extending peripheral slot and moves outwardly in response to impingement of the advancing sleeve with an inclining ramp in the housing adjacent the longitudinally extending peripheral slot in response to the advancing sleeve moving between the first and second positions;
          the advancing sleeve having a bottom rail which slidingly engages the longitudinally extending groove in the housing;
          the advancing sleeve having an expanded rear portion;
    a catheter disposed within a collection bag sleeve;
       the collection bag sleeve sealed about at least one peripheral edge to itself and to the collection bag;
       the collection bag sleeve bonded to at least a portion of a proximal end of the hollow cylindrical housing;
       the collection bag sleeve bonded to at least a portion of the top rail of the advancing sleeve;
       the collection bag sleeve bonded to at least a portion of the bottom rail of the advancing sleeve;

the collection bag sleeve forming an accordion-like configuration when the advancing sleeve is in the first position;

an introducer tip having a front and a rear;

the rear of the introducer tip matingly engaging with the forward-projecting cylinder extension of the housing;

the front of the tip having at least one transversely extending slit;

a front protective cap positioned over at least a portion of the introducer tip; and a rear protective cap positioned over the expanded rear portion of the advancing sleeve.

12. The kit of claim 11 wherein a slope for the inclining ramp for upward deflection is between 1° and 60° inclusive; and a slope for the declining ramp for downward deflection is between 1° and 60° inclusive.

13. The kit of claim 12 wherein the slope for the inclining ramp and the declining ramp are the same.

14. The kit of claim 12 wherein the slope for the inclining ramp and the declining ramp are different.

15. The kit of claim 13 wherein the split front pair of opposed surfaces are essentially semi-circular.

16. The kit of claim 11 wherein:

the rear cap attached to the expanded rear portion of the advancing sleeve has a loop affixed to a periphery of the rear cap.

17. A catheter insertion device which comprises:

a collection bag;

a catheter insertion device, comprising:

a substantially hollow cylindrical housing defining a longitudinally extending peripheral slot on one side of the housing;

the housing defining an opposed longitudinally extending groove opposed from the peripheral slot;

a forward-projecting cylinder extension in communication with the substantially hollow housing; and a means for preventing or retarding rearward motion of the catheter;

a catheter advancing means insertable into the cylindrical housing and having a first proximal position and a second distal position, comprising:

a means for effecting transverse movement of at least one component of the catheter advancing means, the transverse movement effected at least in part to impingement of the advancing means with a declining ramp in the housing adjacent the longitudinally extending peripheral slot and moves outwardly in response to impingement of the advancing means with an inclining ramp in the housing adjacent the longitudinally extending peripheral slot in response to the advancing means moving between the first and second positions;

a catheter disposed within a collection bag sleeve;

the collection bag sleeve sealed about at least one peripheral edge to itself and to the collection bag;

the collection bag sleeve bonded to at least a portion of a proximal end of the hollow cylindrical housing;

the collection bag sleeve bonded to at least a portion of the top rail of the advancing sleeve;

the collection bag sleeve bonded to at least a portion of the bottom rail of the advancing sleeve;

the collection bag sleeve forming an accordion-like configuration when the advancing sleeve is in the first position;

an introducer tip having a front and a rear;

the rear of the introducer tip matingly engaging with the forward-projecting cylinder extension of the housing; and the front of the tip having at least two transversely extending slits.

18. The device of claim 17 wherein the means for effecting transverse movement of at least one component of the catheter advancing means is a pair of laterally extending wings which make contacting engagement with the declining and inclining ramps.

19. The device of claim 18 which further comprises:

a handle on the substantially hollow cylindrical housing, the handle positioned opposite the longitudinally extending peripheral slot of the housing.

20. The device of claim 19 wherein the top rail of the advancing means rides in the longitudinally extending peripheral slot; and the bottom rail of the advancing means rides in the opposed longitudinal extending groove opposed from the longitudinally extending peripheral slot.

* * * * *